US006281368B1

(12) United States Patent
McChesney et al.

(10) Patent No.: US 6,281,368 B1
(45) Date of Patent: Aug. 28, 2001

(54) SIMPLE AND EFFICIENT HYDRAZINOLYSIS OF C-10 AND C-13 ESTER FUNCTIONALITIES OF TAXANES TO OBTAIN 10-DAB III

(75) Inventors: James D. McChesney; Madhavi C. Chander, both of Boulder; Douglas L. Rodenburg, Longmont, all of CO (US)

(73) Assignee: NaPro BioTherapeutics, Inc., Boulder, CO (US)

( * ) Notice: Subject to any disclaimer, the term of this patent is extended or adjusted under 35 U.S.C. 154(b) by 0 days.

(21) Appl. No.: 09/527,007

(22) Filed: Mar. 16, 2000

(51) Int. Cl.[7] .................................................. C07D 305/14
(52) U.S. Cl. ............................................. 549/510; 549/511
(58) Field of Search ....................................... 549/510, 511

(56) References Cited

U.S. PATENT DOCUMENTS

| | | |
|---|---|---|
| 5,202,448 | 4/1993 | Carver et al. . |
| 5,256,801 | 10/1993 | Carver et al. . |
| 5,393,895 | 2/1995 | Gaullier et al. . |
| 5,393,896 | 2/1995 | Gaullier et al. . |
| 5,453,521 | 9/1995 | Gaullier et al. . |
| 5,736,366 | 4/1998 | Margraff . |
| 5,750,736 | 5/1998 | Sisti et al. . |
| 5,914,411 | 6/1999 | Sisti et al. . |
| 6,002,025 | 12/1999 | Page et al. . |

OTHER PUBLICATIONS

"Modified Taxols. 3. Preparation and Acylation of Baccatin III" Journal of Organic Chemistry, Magri et al, 1986 51, 3239–3242.

"Structure–Activity Relationships of Taxol: Synthesis and Biological Evaluation of C2 Taxol Analogs", Bioorg. Med. Chem. Lett., Chen et al, 1994, 4, 479–482.

"Unexpectedly Facile Hydrolysis of the 2–Benzoate Broup of Taxol and Sysntheses of Analogs with Increased Activities", J. Am. Chem. Soc., Chaudhary et al, 1994, 116, 4097 4098.

"Internal Nucleophile Assisted Selective Deesterification Studies on Baccatin III. Synthesis of 2–Debenzoyl—and 4–Decetylbacatin III Analogues", J. Org. Chem., Datta et al, 1994, 59, 4689–4690.

"Selective Deesterification Studies on Taxanes: Simple and Efficient Hydrazinolysis of C–10 and C–13 Ester Functionalities", J. Org. Chem., 1995, 60, 761–63.

*Primary Examiner*—Ba K. Trinh
(74) *Attorney, Agent, or Firm*—Timothy J. Martin; Michael R. Henson; Mark H. Weygandt

(57) ABSTRACT

A process for producing 10-deacetyl baccatin III from an acidic solution containing a spectrum of taxanes, comprising contacting the acidic solution containing the spectrum of taxanes with a hydrazine hydrate, thereby to convert into 10-deacetyl baccatin III some taxanes in said solution that are not 10-deacetyl baccatin III.

46 Claims, No Drawings

SIMPLE AND EFFICIENT HYDRAZINOLYSIS OF C-10 AND C-13 ESTER FUNCTIONALITIES OF TAXANES TO OBTAIN 10-DAB III

FIELD OF THE INVENTION

The present invention generally relates to the purification of a biomass extract to form useful materials. More particularly, the present invention is directed to the conversion of unwanted taxanes in a biomass extract to taxanes that can be used in the synthesis of paclitaxel. Specifically, the present invention relates to the conversion of unwanted taxanes into 10-deacetyl baccatin III, a useful precursor in the formation of paclitaxel.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, including refractory ovarian and metastatic breast cancers. Clinical trials, including those for the treatment of lung, head, neck and other cancers, indicate that paclitaxel promises a broad range of potent anti-leukemic and tumor-inhibiting activity. Further development of this pharmaceutical lead and identification of its superior analogs is crucial to continued advancement of cancer chemotherapy.

Paclitaxel has the formula and numbering as follows:

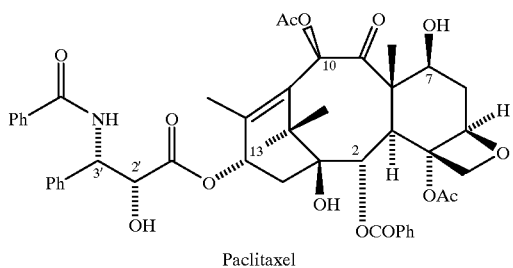

Paclitaxel

Paclitaxel is a naturally occurring taxane diterpenoid which is found in several species of the yew (genus Taxus, family Taxaceae). Unfortunately, the concentration of this compound is very low. The species of evergreen yew are also slow growing. Even though the bark of the yew trees typically exhibit the highest concentration of paclitaxel, the production of one kilogram of paclitaxel requires approximately 16,000 pounds of bark. Thus, the long term prospects for the availability of paclitaxel through isolation are discouraging.

Accordingly, numerous efforts have been directed to the partial synthesis of paclitaxel from closely related precursor compounds. While the presence of paclitaxel in the yew tree is in extremely low concentrations, there are a variety of other taxane compounds, such as Baccatin III, cephalommanine, 10-deacetyl baccatin III, etc., which are also able to be extracted from the yew. Some of these other taxane compounds are more readily extracted in higher yields.

In order to successfully synthesize paclitaxel, convenient access to a chiral, non-racemic side chain and an abundant natural source of a usable baccatin III backbone as well as an effective means of joining the two are necessary. However, the esterification of the side chain to the protected baccatin III backbone is difficult because of the sterically hindered C-13 hydroxyl in the baccatin III backbone which is located within the concave region of the hemispherical protected baccatin III skeleton. Techniques have been developed for the partial synthesis of paclitaxel from the naturally occurring diterpenoid substances baccatin III and closely related 10-deacetyl baccatin III ("10-DAB III"), which accordingly have become important precursors for use in synthetic routes to paclitaxel. Baccatin III and 10-DAB III have the formulas as follows:

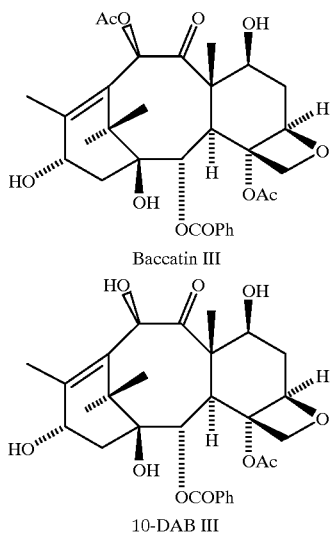

Baccatin III

10-DAB III

10-DAB III is more abundant in nature than is baccatin III. Indeed, a relatively high concentration of 10-DAB III can be extracted from the leaves of the yew as a renewable resource. Co-occurring with paclitaxel, baccatin III and 10-DAB III in biomass are several closely related taxanes containing the same diterpenoid structure element of baccatin III or 10-DAB III. They are removed as side stream products during usual purification procedures for paclitaxel or 10-DAB III. These side stream products include cephalomannine, nitine, taxol C, 7-xylosyl taxols, 10-deacetyl taxol, and several other taxanes and non-taxanes. As shown in Table 1, many of these taxanes have the same general backbone structure as follows:

TABLE 1

| Product | $R_1$ | $R_2$ |
|---|---|---|
| CEPHALOMANNINE | tigloyl | Ac |
| NITINE | phenyl acetyl | Ac |
| TAXOL C | hexanoyl | Ac |
| 10-DEACETYL TAXOL | benzoyl | H |

Although these side stream products have general structures similar to the structures of paclitaxel, baccatin III and 10-DAB III, they are currently left over as unusable waste products of the purification processes for paclitaxel or 10-DAB III. Accordingly, it would be desirable to convert such leftover side stream products into usable materials for paclitaxel synthesis, thereby to increase the availability of this important anti-cancer agent.

Only a few methods have been reported for the selective hydrolysis of the various ester groups present in paclitaxel. Magri et al have reported on the selective reductive cleavage of the C-13 side chain of paclitaxel, using tetrabutyl ammonium borohydride (Journal of Organic Chemistry, 1986, 51, 3239–3242). U.S. Pat. Nos. 5,202,448 and 5,256,801 to Carver et al. teach the conversion of partially purified taxane mixtures into baccatin III and 10-DAB III using a borohydride reducing salt in the presence of a Lewis acid.

The selective hydrolysis of the benzoate group at C-2 has been achieved by three research groups. In one method by Chen et al, a 7,13-diprotected baccatin III with Red-Al afforded the corresponding 2-debenzoylated derivative in 78% yield (Bioorg. Med. Chem. Lett. 1994, 4, 479–482). In another method, reported by Chaudhary et al, hydrolysis of 2', 7-diprotected paclitaxel with NaOH under phase transfer conditions formed the corresponding 2-debenzoylpaclitaxel derivative in moderate yield (J. Am. Chem. Soc., 1994, 116, 4097). In a third method, reported by Datta et al, selective deesterification of baccatin III derivatives at C-2 and C-4 was achieved in 69% and 58% yields respectively with potassium tert-butoxide as base (J. Org. Chem., 1994, 59, 4689–4690).

Appurba Datta, Michael Hepperle, and Gunda I. Georg have also reported, in J. Org. Chem, 1995, 60, 761–63, selective deesterification processes to remove the C-10 and C-13 ester funtionalities of pure cephalomannine and paclitaxel by hydrazinolysis. That work was encouraged by a recognition that both ammonia and hydrazine are used for the removal of ester groups under mild conditions wherein acetates are preferentially cleaved over benzoate groups. Datta, Hepperle and Georg reported that a solution of paclitaxel in 95% ethanol that was treated with hydrazine monohydrate at room temperature for two hours yielded 10-DAB III as the only product obtained. The 10-DAB III product was formed by cleavage of the ester linkages of paclitaxel at C-10 and C-13. Datta, Hepperle and Georg extended this reaction to a National Cancer Institute mixture of mainly paclitaxel and cephalomannine with some other minor impurities, which cleanly yielded 10-DAB III when reacted with hydrazine monohydrate. The reactions reported by Datta, Hepperle and Georg utilizing a hydrazine monohydrate solution in 95% ethanol were at a pH of about 10, such that the hydrazine monohydrate, a strong base, is reactive to cleave ester groups similarly to other basic nucleophiles.

However, there remains a need to provide simple and efficient methods to convert sidestream products from extraction processes, which generally result in highly acidic biomass extracts, into usable products such as 10-DAB III. In particular, there remains a need for a process to convert a complex mixture of taxanes, such as one containing cephalomannine, 10-deacetyl taxol, baccatin III and several other taxanes in a relatively unpurified or partially purified form, to 10-DAB III which can be purified and utilized for semi-synthesis purposes to synthesize paclitaxel and its analogs. The present invention is directed to meeting these needs.

SUMMARY OF THE INVENTION

It is an object of the present invention to provide a new and useful process for the conversion of sidestream products from taxane extraction processes into usable products for paclitaxel synthesis.

It is another object to provide a simple and efficient method to convert a complex mixture of taxanes into paclitaxel precursor products.

It is yet another object to produce useful synthetic precursors from an acidic biomass extract.

A still further object is to produce relatively pure 10-DAB III from a mixture of taxanes such as cephalomannine, 10-deacetyltaxol, baccatin III and several other taxanes.

Yet another object is to produce 10-DAB III useful in paclitaxel synthesis from a biomass extract containing taxanes that have ester functionalities at the C-10 and/or C-13 positions.

According to the present invention, a process for producing 10-deacetyl baccatin III from a relatively unpurified or partially purified mixture of taxanes comprises contacting a solution containing a spectrum of taxanes, which may include at least three distinct taxanes, with a hydrazine hydrate, preferably hydrazine monohydrate, thereby to convert into 10-deacetyl baccatin III some taxanes in the solution that are not 10-deacetyl baccatin III. The solution may be produced by contacting a biomass extract, which may be adsorbed onto a suitable substrate, with a solvent, preferably an alcohol and most preferably methanol. The biomass extract is derived from a plant of the genus Taxus, and may be partially purified by partitioning between organic and aqueous layers. The solution may be produced by contacting the biomass extract with the solvent prior to any purification of the biomass extract by HPLC. The solution may include organic plant acids such that it may be generally acidic, and may specifically have a pH of 3–4. 7-acetyl baccatin III may be added to the solution prior to the step of contacting the solution with a hydrazine hydrate.

It is preferred that the hydrazine monohydrate is approximately 64% by weight hydrazine and the solution is contacted with approximately 2.0 mL of hydrazine monohydrate per 1.0 g of solution. After the step of contacting the solution with a hydrazine hydrate, 10-deacetyl baccatin III may be recovered from said solution by partitioning between an organic layer, such as isobutyl acetate, and an aqueous layer. Alternatively, the solution may be quenched with a suitable quenching agent, which may be a dilute acid solution or an aqueous ammonium chloride solution. The organic layer may be passed through an adsorption column, and 10-deacetyl baccatin III may thereafter be crystallized from said organic layer using acetonitrile as an anti-solvent.

The present invention also includes a process for producing 10-deacetyl baccatin III from a biomass extract that contains as a constituent thereof at least one taxane that has an ester functionality on at least one of the C-10 and C-13 positions. The process comprises contacting the biomass extract with an appropriate solvent therefor, thereby to form a solution that contains at least one taxane solute that has an ester functionality on at least one of the C-10 and C-13 positions, and thereafter contacting the solution with a hydrazine hydrate, preferably hydrazine monohydrate, thereby to cleave the ester functionality of the taxane solute. The biomass extract may be adsorbed onto a suitable substrate prior to the step of contacting the biomass extract with the solvent, and the step of contacting the biomass extract with the solvent may occur prior to any purification of the biomass extract by HPLC. The solution may include organic plant acids such that it is acidic, and may have a pH of 3–4. The solution may contain less than five (5) weight percent of taxanes.

Additionally, the present invention is directed to a process for producing 10-deacetyl baccatin III from a biomass extract derived from a plant of the genus Taxus, which comprises contacting the biomass extract with a mixture of a solvent, preferably methanol, and a hydrazine hydrate, preferably hydrazine monohydrate, thereby to convert into 10-deacetyl baccatin III some taxanes in the biomass extract that are not 10-deacetyl baccatin III. The biomass extract may be adsorbed onto a suitable substrate prior to the step of contacting the biomass extract with the mixture. The biomass extract may be contacted with the mixture prior to any purification of the biomass extract by HPLC.

The present invention additionally includes a process for converting a baccatin III analog having an ester functionality at the C-7 position thereof, such as 7-acetyl baccatin III, into 10-deacetyl baccatin III. The process comprises contacting a solution containing the baccatin III analog as a constituent thereof with a hydrazine hydrate, thereby to form 10-deacetyl baccatin III.

These and other objects of the present invention will become more readily appreciated and understood from a consideration of the following detailed description of the exemplary embodiments of the present invention

DETAILED DESCRIPTION OF THE EXEMPLARY EMBODIMENTS

The present invention discloses a surprising result not suggested by the work of Datta, Hepperle and Georg, discussed above, which was reported in "Selective Deesterification Studies on Taxanes: Simple and Efficient Hydrazinolysis of C-10 and C-13 Ester Functionalities", J. Org. Chem, 1995, 60, 761–63. As reported therein, alkaline solutions of purified taxanes were converted to 10-DAB III by selective deesterification of the C-10 and C-13 ester functionalities. Datta, Hepperle and Georg reported that 0.5 mL hydrazine monohydrate was added to a pure solution of 35 mg paclitaxel in 95% ethanol (5mL). This solution had a pH of 10 such that hydrazine monohydrate, which is a strong base, was not neutralized. The mixture was stirred at room temperature for 2 hours, then diluted with 50 mL ethyl acetate and poured into saturated ammonium chloride solution. The organic layer was separated, washed with water and brine, dried with sodium sulfate, concentrated, and the residue was purified by flash column chromatography yielding 10-DAB III in 82% yield. Datta, Hepperle and Georg also reported the above process performed upon a National Cancer Institute mixture, which is provided as a clean white powder of primarily purified paclitaxel and cephalomannine. The work of Datta, Hepperle and Georg suggests that a highly alkaline solution of pure taxanes is necessary for the selective C-10 and C-13 deesterification of taxanes by hydrazinolysis.

Surprisingly, we have observed that a complex mixture of taxanes containing cephalomannine, 10-deacetyl taxol, baccatin III and several other taxanes in an unpurified form derived from biomass may be converted with hydrazine hydrate to 10-DAB III, which is purified and utilized for the semi-synthesis of paclitaxel and its analogs. This conversion is unexpected due to the presence of acidic biomass derived substances present in the unpurified process side streams that contain taxanes. These acidic biomass derived substances should greatly reduce or quench any hydrazine reactivity toward esters. In particular, this process provides a surprising result in that it would be expected that hydrazine hydrate, which is a strong base, would be neutralized upon addition to an acidic extract solution of a Taxus biomass extract. Accordingly, our process provides an unexpected yet efficient route to utilize the byproduct side stream taxanes without tedious purification procedures and to convert these taxanes to an essential taxane, 10-DAB III, the building block for semi-synthesis of paclitaxel.

I. Preparation of Biomass Extract

The present invention utilizes biomass extract, which may be partially or minimally purified, and which is derived from a plant of the genus Taxus. Specifically, the biomass extract may be derived from yew varieties such as *Taxus baccata, Taxus brevifolia, Taxus canadensis, Taxus cuspidata, Taxus floridana, Taxus media* and *Taxus wallichiana*. Such biomass extracts contain various taxanes, such as cephalomannine, 10-deacetyl taxol, baccatin III and other taxanes, as well as a range of other materials, such as plant materials including phenolic materials and carboxylic acids. Generally, the biomass extract is composed of only a few weight percent, such as approximately five percent (5%), taxanes. The remainder is composed of other biomass derived substances such as acidic plant materials. The biomass extracts used in the present invention are generally aqueous alcohol extracts of Taxus biomass that have been treated to remove therefrom some plant materials such as chlorophyl and plant pigments, as well as the majority of paclitaxel.

The production of such biomass extracts is commonly known in the art. Exemplary methods for producing biomass extracts for use in the present invention are described in part, for example, in U.S. Pat. No. 5,393,895 to Gaullier et al., and U.S. Pat. Nos. 5,393,896 and 5,736,366 to Margraff. The teachings of those references are incorporated herein by reference. In particular, as discussed in the Gaullier et al. patent, one process for the production of biomass extracts for use in the present invention begins with stirring an optionally heated mixture of ground yew vegetable matter and an aliphatic alcohol, such as methanol, to obtain an alcoholic extract. The ground yew vegetable matter may be derived from any appropriate part of the yew, and may be obtained by grinding and optionally drying operations to obtain fragments of yew. In obtaining such fragments, freezing and thawing operations directed to the fresh parts of the plant may be optionally utilized as well.

The alcoholic extract, which may first be concentrated, is next diluted with water to form a hydroalcoholic solution. Products that are insoluble in the hydroalcoholic solution are then removed, such as by filtration, centrifugation or settling. Virtually all of the alcohol is then removed from the hydroalcoholic solution, such as by distillation at reduced pressure. The remaining aqueous solution is then extracted with an organic solvent, such as an ether or aliphatic ester, the organic extract is optionally washed with water and/or an aqueous solution of a weak base, and dried. The organic solvent is next removed, such as by distillation at reduced pressure, to produce a residue.

The remaining residue constitutes a biomass extract for use in the hydrazinolysis reaction described below. It should be appreciated that this biomass extract contains 10-DAB III as well as taxane constituents having an ester functionality on at least one of the C-10 and C-13 positions, such as cephalomannine, 10-deacetyl taxol, baccatin III and other taxanes. It has been found that 10-DAB III is stable under the reaction conditions for the hydrazinolysis reaction described below, such that the present invention makes it possible to obtain good yields of 10-DAB III from yew vegetable matter without requiring an extra step of first isolating and removing any 10-DAB III extracted by the above process.

Additional processes for the production of biomass extracts for use in the present invention are discussed, for example, in the Margraff patents. Although generally similar to the process taught by Gaullier et al., Margraff teaches that ground yew vegetable matter is first stirred with water, such as at a temperature of 20° to 65° C. for a time interval of 30 minutes to 2 hours. The aqueous solution obtained is then separated from the vegetable matter remaining in suspension, such as by filtration, centrifugation or settling, and optionally may be cooled.

Taxanes may next be extracted from the aqueous solution by adding an organic solvent thereto, such as an ether or aliphatic ester. The organic extract is separated from the aqueous phase, is optionally washed with water and/or an aqueous solution of a weak base, and dried, after which the organic solvent is removed, such as by distillation at reduced pressure, to produce a residue.

As an alternative to extraction, the aqueous solution may be adsorbed on a suitable substrate, such as an adsorbing resin, which is then washed with a suitable solvent, such as methanol. The resulting solution is then separated from the substrate, such as by filtration, and concentrated to dryness, such as by distillation at reduced pressure, to produce a residue.

As with the residue produced according to the teachings of the Gaullier et al. reference, such a residue produced according to either of the processes taught by the Margraff references constitutes a biomass extract for use in the hydrazinolysis reaction described below. Again, it should be appreciated that this biomass extract contains 10-DAB III as well as taxane constituents having an ester functionality on at least one of the C-10 and C-13 positions.

Alternatively, as discussed in the Gaullier et al. and Margraff references, 10-DAB III may first be removed from the residue prior to the hydrazinolysis reaction described below. This is accomplished by selective crystallization of 10-DAB III from a solution of the residue in one or more organic solvents, which may include acetonitrile. The 10-DAB III precipitate is separated from the residue solution, such as by filtration, centrifugation or settling. The solution remaining after the removal of the 10-DAB III forms an alternative biomass extract for use in the hydrazinolysis reaction of the present invention. Additionally, the solution remaining after the removal of 10-DAB III may be concentrated, such as by distillation at reduced pressure, to form a further alternative version of the biomass extract.

It should be appreciated that after the removal of 10-DAB III, the resulting biomass extract still contains taxane constituents having an ester functionality on at least one of the C-10 and C-13 positions, such as cephalomannine, 10-deacetyl taxol, baccatin III and other taxanes. Furthermore, it should be noted that, while a biomass extract resulting from the above processes may have been partially purified by partitioning between organic and aqueous layers, it has not been subjected to purification by HPLC. In particular, the process of the present invention is desirable in that it minimizes the need for such additional purification steps, thus affording an attractive and efficient route to recovering and using otherwise unusable taxanes.

II. Production and Purification of 10-DAB III from Biomass Extract

The present invention provides an efficient method for the selective transformation of a complex mixture of taxanes by deesterification of the C-10 and C-13 ester functionalities thereof. The process utilizes biomass extract produced as sidestream products from taxane extraction processes, such as described above.

A. Hydrazinolysis Reaction

An exemplary reaction according to the present invention is as follows:

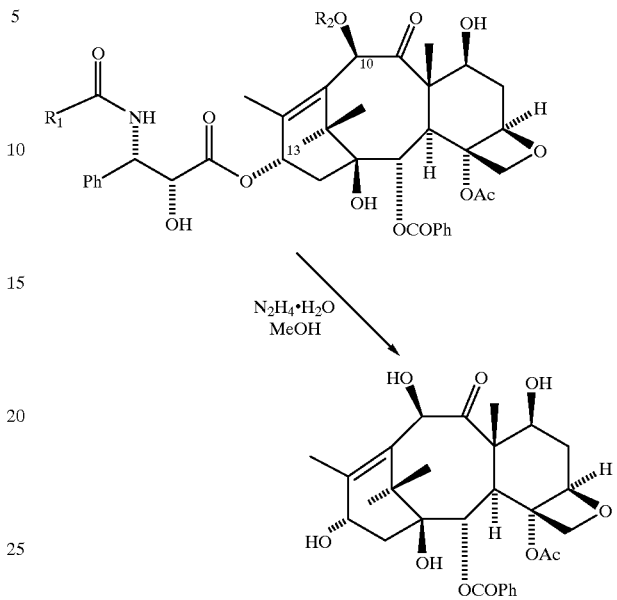

wherein $R_1$ can be an alkyl group, an olefinic group, an aromatic group, hydrogen or a group containing oxygen, nitrogen or sulfur; and $R_2$ can be hydrogen or $R_3C\!\!=\!\!O$ wherein $R_3$ is an alkyl group. $R_1C\!\!=\!\!O$ can specifically be benzoyl, tigloyl, phenyl acetyl, or hexanoyl, and $R_3C\!\!=\!\!O$ can specifically be acetyl.

As demonstrated in the above reaction, the ester functionalities at the C-10 and C-13 positions are cleaved by hydrazinolysis. It should be understood that where the C-10 position includes a hydroxyl group bonded thereto (i.e., $R_2$ is H) such that no C-10 ester functionality is present, only the C-13 side chain is affected. Furthermore, it should be appreciated that the above-illustrated chemical structures are not exhaustive of all possible moieties for taxanes found in biomass extract that have the general taxane backbone found in 10-DAB III, and which may be reacted according to the present invention.

In the preferred embodiment, a solution is formed containing a spectrum of taxanes having ester functionalities at the C-10 position, C-13 position or both. This solution is formed by contacting a biomass extract prepared as described above with an appropriate solvent therefor, preferably an alcohol and most preferably methanol. In particular, it is preferred that the methanol extraction is performed on biomass extract that is adsorbed onto silica gel and packed in a column. It should be appreciated that silica gel may be substituted with other suitable substrates, such as silica, sand, diatomaceous earth or other high surface area non-reactive substrates. The solution thus formed is acidic in nature, generally having a pH in the range of 3–4, as the result of organic plant acids present therein. Alternatively, the solvent may be directly mixed with the biomass extract to form the acidic solution. In any event, the weight percent of taxanes in the solution is generally less than five percent (5%). The solution is preferably concentrated to a ratio of 1.0 mL/0.15 g of total dissolved solids using a rotary evaporator at $\leq 55°$ C. To this solution is added a hydrazine hydrate, preferably hydrazine monohydrate (64% hydrazine by weight), at a preferred ratio of 2.0 mL/1 g of total dissolved solids present in the solution. The resulting reaction mixture is stirred at ambient temperature for 3 hours under a $N_2$ blanket.

Several ratios of hydrazine hydrate to total dissolved solids have been tested. In particular, 3, 4 and 5 hour reactions were performed at varying ratios of between 0.6 mL and 4.0 mL hydrazine hydrate to total dissolved solids at solvent to total dissolved solids solution concentrations of 1 mL methanol to between 0.1 g and 0.15 g total dissolved solids. These reactions were performed using partially purified methanolic extracts of Taxus biomass. To monitor the reaction rate, the concentration of 10-deacetyl taxol expressed as a relative area percent of 10-DAB III was measured.

Specifically, the reaction rates and 10-DAB III yield were measured for 4 and 5 hour reactions at a 0.6 mL hydrazine monohydrate/g total dissolved solids ratio, and for 3 hour reactions at ratios of 0.6 mL, 1.0 mL, 1.2 mL, 1.9 mL, 2.0 mL, 2.4 mL, 3.0 mL and 4.0 mL hydrazine hydrate/g total dissolved solids. It was found that too low of a hydrazine hydrate to total dissolved solids ratio resulted in a longer time period for complete reaction, whereas too high of a hydrazine hydrate to total dissolved solids ratio resulted in lower 10-DAB III yields. It should be appreciated that in commercial processes, shorter reaction times are desirable to the extent that acceptable yields are maintained. The preferred balance of reaction rate and 10-DAB III yield was found using a 2.0 mL hydrazine hydrate/g total dissolved solids ratio at a solution concentration of 1 mL methanol/ 0.15 g total dissolved solids, which allowed a reaction duration of 3 hours.

It should further be appreciated that the present invention contemplates a hydrazinolysis reaction wherein the biomass extract is directly contacted with a mixture of a solvent, preferably methanol, and a hydrazine hydrate, preferably hydrazine monohydrate. It is believed that in such a case the hydrazine hydrate will cleave the C-10 and C-13 ester functionalities of taxanes present in the biomass extract, thereby to convert such taxanes into 10-DAB III. The biomass extract may alternatively be adsorbed onto a suitable substrate prior to being contacted with the mixture.

B. Recovery and Purification of 10-DAB III

At the end of the time interval for the hydrazinolysis reaction, such as the 3 hour period in the example above, the reaction mixture is preferably partitioned between isobutyl acetate and water to separate the 10-DAB III from the hydrazine and dissolved solids. Alternatively, the solution may be quenched with a suitable quenching agent, such as with a dilute acid solution or aqueous ammonium chloride solution, although this quenching step can increase the time requirement for the total process by 3 to 5 hours. When the hydrazinolysis reaction is not quenched, it is preferred that the reaction is partitioned quickly to separate the hydrazine from the taxanes. It is believed that reactions that are not partitioned quickly could result in lower 10-DAB III yields, as a result of decomposition of some 10-DAB III in the solution, because the reaction of hydrazine with the taxanes will continue until the hydrazine is separated therefrom.

Preferably, the partitioning occurs by first mixing isobutyl acetate and the reaction solution, then adding water. It is preferred that an amount of water is added that is equal to 45% of the reaction solution volume less the amount of water in the hydrazine hydrate. The ratio of isobutyl acetate is preferably 1 mL per 1 mL of the reaction mixture and water combined. The combined reaction mixture and isobutyl acetate are agitated well for at least 1 hour, the agitation stopped and the layers allowed to separate for at least 30 minutes. It should be recognized that the taxanes are partitioned into the top organic isobutyl acetate layer and the hydrazine and any salts that are formed are partitioned into the bottom aqueous layer, although a small percentage of 10-DAB III may remain in the aqueous layer. The organic layer is separated and the aqueous layer is preferably re-extracted with an equal volume of isobutyl acetate in the same manner as above, to recover any 10-DAB III remaining in the aqueous layer.

The isobutyl acetate layers resulting from the above partitioning steps are combined and preferably passed through a carbon/alumina/silica adsorption column to reduce total dissolved solids and color. The use of an adsorption column after the hydrazinolysis and prior to the crystallization steps outlined below assists in maximizing the 10-DAB III yield through the prevention of precipitate formation during concentration for crystallization. The column preferably contains layers of granular activated carbon, alumina N1 and silica gel in this order from top to bottom. The preferred ratios are 0.5 g of carbon, 1.0 g of alumina N1 and 1.0 g of silica gel per 1.0 g of total dissolved solids in the isobutyl acetate solution. After passing the isobutyl acetate extract through the column in a downward flow, the column is preferably eluted with approximately three (3) column volumes of isobutyl acetate and the rinse combined with the solution.

The resulting solution is preferably concentrated on a rotary evaporator at $\leq 55°$ C. to a total dissolved solids residue of approximately 0.3 g/mL and acetonitrile (MeCN) is preferably added (approximately 10% of the total volume) as an anti-solvent, such that a crystallization of the 10-DAB III in isobutyl acetate with acetonitrile may be performed. The low solubility of 10-DAB III in acetonitrile, contrasted with good solubility of most other compounds in acetonitrile, makes it an ideal anti-solvent for 10-DAB III crystallizations. The resulting mixture is stirred at ambient temperature for at least five (5) hours during which time a solid precipitate forms. The solid obtained is filtered and the filter cake washed with 9:1 isobutyl acetate and acetonitrile solution at a ratio of 1.0 mL/1.0 g of total dissolved solids.

The washed solid is preferably dissolved in methanol at a ratio of 30 mL/1.0 g of total dissolved solids in the isobutyl acetate concentrate, and this solution is filtered through a 1 μm filter. The filtered methanol solution is preferably concentrated on a rotary evaporator at $\leq 55°$ C. to a residue of approximately 0.133 g/mL and a crystallization of the 10-DAB III in methanol with acetonitrile as an anti-solvent is performed by adding acetonitrile (40% of the total volume) at ambient temperature with continuous stirring for five (5) hours. The solid formed is filtered and the filter cake washed with methanol and acetonitrile (7:3, v:v) at a ratio of 4 mL/1.0 g of total dissolved solids in the methanol solution. The solid is dried in a vacuum oven at $\leq 80°$ C. for at least sixteen (16) hours to reduce the concentration of residual methanol to $\leq 0.5\%$ by weight. Such a reduction of methanol is desirable in that methanol has been found to interfere with the acetylation of 10-DAB III in the paclitaxel synthetic process.

The 10-DAB III at this stage is >95% by HPLC area and is suitable as a starting material for the semi-synthesis of paclitaxel. It should be noted that 10-DAB III mother liquors and rinses resulting from the above purification steps can be recycled using multiple methanol/acetonitrile crystallizations, to increase the overall 10-DAB III yield.

III. Hydrazinolysis of 7-Acetyl Baccatin III

U.S. Pat. No. 5,750,736 to Sisti and U.S. Pat. No. 5,914, 411 to Sisti et al. each disclose a method for acylating 10-DAB III selectively at the C-10 position over the C-7 position to form baccatin III. As shown in U.S. Pat. No. 5,750,737 to Sisti et al., baccatin III is a precursor compound in the semi-synthesis of paclitaxel. However, 7-acetyl baccatin III is one of the major side-products generated by the acetylation of 10-DAB III during the semi-synthetic process to produce paclitaxel. In order to maximize the use of 10-DAB III in paclitaxel semi-synthesis, it is desirable to recycle and capture this side-product for its 10-DAB III component. It has been discovered that 7-acetyl baccatin III, which can be removed from the paclitaxel semi-synthesis process by normal phase chromatography, can be converted back to 10-DAB III through hydrazinolysis.

In the preferred process, 7-acetyl baccatin III with a 4,000 relative area percent to 10-DAB III was dissolved in methanol in a ratio of 0.1 g/mL. Hydrazine hydrate was added to this solution in a ratio of 2 mL/1 g total dissolved solids. The reaction was run for 3 hours, at the end of which, the 7-acetyl baccatin III concentration was 1.4 relative area percent. These results indicate that hydrazinolysis of 7-acetyl baccatin III cleaves the acetate group from both C-7 and C-10, thereby to convert it to 10-DAB III. Additionally, it is believed that 10-DAB III may be produced by hydrazinolysis of other baccatin III analogs having C-7 ester functionalities.

These results indicate that 7-acetyl baccatin III, as well as other baccatin III analogs having C-7 ester functionalities, can be included in or combined with the solvent (e.g., methanol) extracted biomass extract solution prior to the addition of hydrazine hydrate for the hydrazinolysis reaction described above, thereby to efficiently produce 10-DAB III therefrom.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

We claim:

1. A process for producing 10-deacetyl baccatin III from an acidic solution containing a spectrum of taxanes, comprising contacting the acidic solution containing the spectrum of taxanes with a hydrazine hydrate, thereby to convert into 10-deacetyl baccatin III some taxanes in said solution that are not 10-deacetyl baccatin III.

2. A process according to claim 1 wherein said solution is produced by contacting a biomass extract that is derived from a plant of the genus Taxus with an appropriate solvent therefor.

3. A process according to claim 2 wherein said biomass extract is adsorbed onto a suitable substrate prior to contacting said biomass extract with said solvent.

4. A process according to claim 3 wherein said substrate is silica gel.

5. A process according to claim 2 wherein said biomass extract is partially purified by partitioning between organic and aqueous layers.

6. A process according to claim 2 wherein said solution is produced by contacting said biomass extract with said solvent prior to any purification of said biomass extract by HPLC.

7. A process according to claim 2 wherein said solvent is an alcohol.

8. A process according to claim 2 wherein said solvent is methanol.

9. A process according to claim 1 wherein said solution has a pH of 3–4.

10. A process according to claim 1 wherein said solution includes organic plant acids.

11. A process according to claim 1 wherein 7-acetyl baccatin III is added to said solution prior to the step of contacting the solution with a hydrazine hydrate.

12. A process according to claim 1 wherein said spectrum of taxanes includes at least three distinct taxanes.

13. A process according to claim 1 wherein said hydrazine hydrate is hydrazine monohydrate.

14. A process according to claim 13 wherein said hydrazine monohydrate is approximately 64% by weight hydrazine and wherein said solution is contacted with approximately 2.0 mL of hydrazine monohydrate per 1.0 g of total dissolved solids in said solution.

15. A process according to claim 1 wherein said solution is quenched with a suitable quenching agent after the step of contacting said solution with a hydrazine hydrate.

16. A process according to claim 15 wherein said quenching agent is selected from the group consisting of a dilute acid solution and aqueous ammonium chloride solution.

17. A process according to claim 1 wherein, after the step of contacting said solution with a hydrazine hydrate, 10-deacetyl baccatin III is recovered from said solution by partitioning between an organic and aqueous layer.

18. A process according to claim 17 wherein said organic layer is isobutyl acetate.

19. A process according to claim 17 wherein said organic layer is passed through an adsorption column.

20. A process according to claim 19 wherein 10-deacetyl baccatin III is crystallized from said organic layer using acetonitrile as an anti-solvent.

21. A process for producing 10-deacetyl baccatin III from an acidic biomass extract that contains as a constituent thereof at least one taxane that has an ester functionality on at least one of the C-10 and C-13 positions, comprising:
(a) contacting the biomass extract with an appropriate solvent therefor, thereby to form an acidic solution that contains at least one taxane solute that has an ester functionality on at least one of the C-10 and C-13 positions; and
(b) contacting said solution with a hydrazine hydrate, thereby to cleave the ester functionality of said taxane solute.

22. A process according to claim 21 wherein said biomass extract is adsorbed onto a suitable substrate prior to the step of contacting the biomass extract with said solvent.

23. A process according to claim 22 wherein said substrate is silica gel.

24. A process according to claim 21 wherein the step of contacting the biomass extract with said solvent occurs prior to any purification of the biomass extract by HPLC.

25. A process according to claim 21 wherein said solution has a pH of 3–4.

26. A process according to claim 21 wherein said solution includes organic plant acids.

27. A process according to claim 21 wherein said solution contains less than five (5) weight percent of taxanes.

28. A process according to claim 21 wherein said hydrazine hydrate is hydrazine monohydrate.

29. A process for producing 10-deacetyl baccatin III from a biomass extract derived from a plant of the genus Taxus, comprising contacting the biomass extract with a mixture of a solvent and a hydrazine hydrate, thereby to convert into 10-deacetyl baccatin III some taxanes in the biomass extract that are not 10-deacetyl baccatin III.

30. A process according to claim 29 wherein said biomass extract is adsorbed onto a suitable substrate prior to the step of contacting said biomass extract with said mixture.

31. A process according to claim 30 wherein said substrate is silica gel.

32. A process according to claim 29 wherein said biomass extract is contacted with said mixture prior to any purification of said biomass extract by HPLC.

33. A process according to claim 29 wherein said solvent is methanol and said hydrazine hydrate is hydrazine monohydrate.

34. A process for converting a baccatin III analog having an ester functionality at the C-7 position thereof into 10-deacetyl baccatin III, comprising contacting a solution containing the baccatin III analog as a constituent thereof with a hydrazine hydrate, thereby to form 10-deacetyl baccatin III.

35. A process according to claim 34 wherein said baccatin III analog is 7-acetyl baccatin III.

36. A process for producing 10-deacetyl baccatin III from an acidic solution containing a spectrum of taxanes, comprising contacting the acidic solution containing a spectrum of taxanes with from 0.6 mL to 4.0 mL of a hydrazine hydrate per 1 g total dissolved solids in said solution, thereby to convert into 10-deacetyl baccatin III some taxanes in said solution that are not 10-deacetyl baccatin III.

37. A process according to claim 36 wherein said solution has a pH of 3–4.

38. A process according to claim 37 wherein said solution is contacted with 2.0 mL of hydrazine monohydrate per 1 g total dissolved solids in said solution.

39. A process according to claim 38 wherein said hydrazine monohydrate is approximately 64% by weight hydrazine.

40. A process for producing 10-deacetyl baccatin III from a biomass extract that contains as a constituent thereof at least one taxane that has an ester functionality on at least one of the C-10 and C-13 positions, comprising:
   (a) contacting the biomass extract with an appropriate solvent therefor, thereby to form a solution that contains at least one taxane solute that has an ester functionality on at least one of the C-10 and C-13 positions; and
   (b) contacting said solution with from 0.6 mL to 4.0 mL of a hydrazine hydrate per 1 g total dissolved solids in said solution, thereby to cleave the ester functionality of said taxane solute.

41. A process according to claim 40 wherein said hydrazine hydrate is hydrazine monohydrate that is approximately 64% by weight hydrazine.

42. A process according to claim 40 wherein said solution has a pH of 3–4 prior to contacting said solution with said hydrazine hydrate.

43. A process according to claim 40 wherein said solution is concentrated to a concentration of from 0.1 g to 0.15 g total dissolved solids in said solution per 1 mL of solvent prior to contacting said solution with said hydrazine hydrate.

44. A process according to claim 43 wherein said solvent is methanol.

45. A process for producing 10-deacetyl baccatin III from a biomass extract that contains as a constituent thereof at least one taxane that has an ester functionality on at least one of the C-10 and C-13 positions, comprising:
   (a) contacting the biomass extract with an alcohol solvent, thereby to form a solution having a pH of 3–4 and that contains at least one taxane solute that has an ester functionality on at least one of the C-10 and C-13 positions;
   (b) concentrating said solution to a concentration of from 0.1 g to 0.15 g total dissolved solids in said solution per 1 mL of solvent; and
   (c) contacting said solution with from 0.6 mL to 4.0 mL of hydrazine monohydrate per 1 g total dissolved solids in said solution, thereby to cleave the ester functionality of said taxane solute.

46. A process for producing 10-deacetyl baccatin III from a biomass extract derived from a plant of the genus Taxus, wherein said biomass extract contains organic plant acids, comprising contacting the biomass extract with a mixture of a solvent and a hydrazine hydrate prior to any purification of said biomass extract by HPLC, thereby to convert into 10-deacetyl baccatin III some taxanes in the biomass extract that are not 10-deacetyl baccatin III.

* * * * *